United States Patent [19]
Barthe et al.

[11] Patent Number: 6,120,452
[45] Date of Patent: Sep. 19, 2000

[54] APPARATUS FOR THREE DIMENSIONAL IMAGING

[75] Inventors: Peter G. Barthe, Phoenix; Michael H. Slayton, Tempe, both of Ariz.

[73] Assignee: Guided Therapy Systems, Inc., Mesa, Ariz.

[21] Appl. No.: 09/434,078

[22] Filed: Nov. 5, 1999

Related U.S. Application Data

[62] Division of application No. 09/113,227, Jul. 10, 1998.

[51] Int. Cl.⁷ ........................................... A61B 8/14
[52] U.S. Cl. ............................................. 600/459
[58] Field of Search ..................... 128/916; 600/443, 600/447, 459, 440, 441; 73/633, 634

[56] References Cited

U.S. PATENT DOCUMENTS

| | | |
|---|---|---|
| 5,070,879 | 12/1991 | Herres . |
| 5,088,495 | 2/1992 | Miyagawa . |
| 5,159,931 | 11/1992 | Pini . |
| 5,375,602 | 12/1994 | Lancee et al. ........................... 600/462 |
| 5,398,689 | 3/1995 | Connor et al. ........................... 600/459 |
| 5,417,216 | 5/1995 | Tanaka . |
| 5,622,175 | 4/1997 | Sudol et al. ............................. 600/459 |
| 5,662,116 | 9/1997 | Kondo et al. . |

*Primary Examiner*—Marvin M. Lateef
*Assistant Examiner*—Ali M. Imam
*Attorney, Agent, or Firm*—Snell & Wilmer, L.L.P.

[57] ABSTRACT

A method and apparatus for medical diagnostic ultrasound imaging that utilizes a one, one and one-half or two dimensional scanhead for performing three dimensional imaging. The method and apparatus limits acoustic reverberations by swinging or rotating an array of ultrasound transducer elements about the longitudinal axis of the probe of an ultrasound transducer apparatus to enable the transducers to maintain a constant and concentric position with the acoustic membrane of the probe.

14 Claims, 3 Drawing Sheets

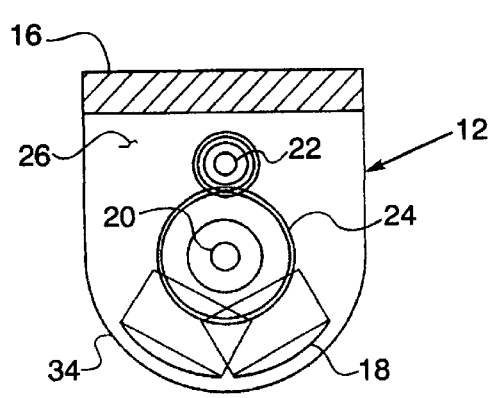
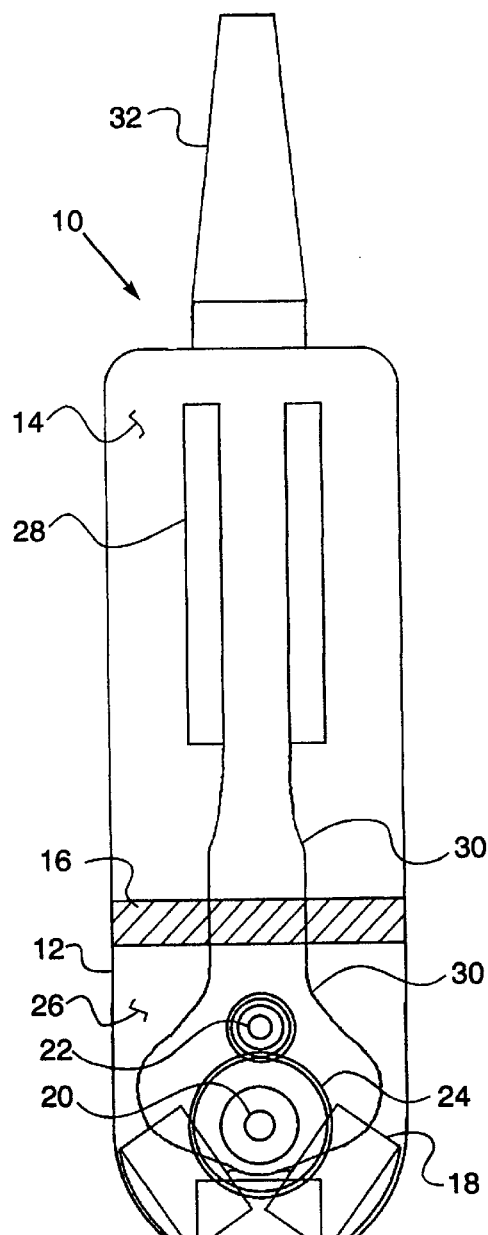
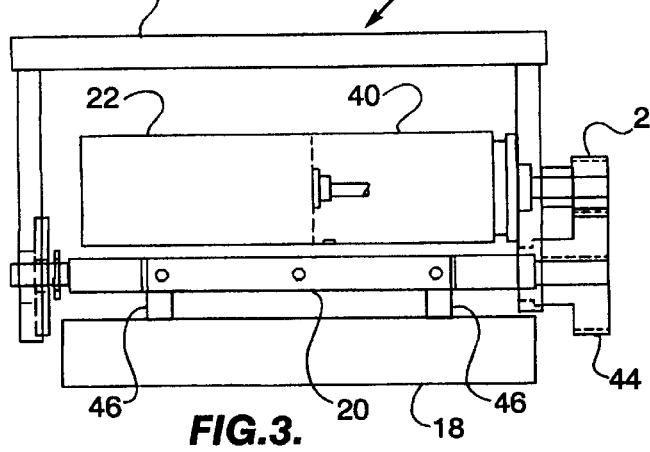
FIG.1.
FIG.2.
FIG.3.
FIG.4.

ABSTRACT# APPARATUS FOR THREE DIMENSIONAL IMAGING

REFERENCE TO RELATED DOCUMENTS

This application is a divisional application of U.S. patent application Ser. No. 09/113,227, filed Jul. 10, 1998 and entitled "METHOD AND APPARATUS FOR THREE DIMENSIONAL ULTRASOUND IMAGING".

FIELD OF THE INVENTION

The present invention generally relates to a method and apparatus for ultrasound imaging for medical diagnostic procedures that utilizes a one, one and one half, or two dimensional scanhead for performing three dimensional imaging. More particularly, the present invention is directed to a method and apparatus for diagnostic ultrasound imaging which includes the act of swinging or rotating an array of ultrasound transducer elements about the longitudinal axis of a shaft at a predetermined distance from the shaft, to enable the transducers to maintain a constant distance from the membrane throughout the swing or rotation of the transducers. This method of ultrasound imaging limits acoustic reverberations during imaging thereby decreasing unusable images.

BACKGROUND OF THE INVENTION

The rotating of ultrasound transducer arrays contained in ultrasound imaging apparatus in order to produce three-dimensional images is common in the prior art. For example, U.S. Pat. No. 5,662,116 issued to Kondo et al. discloses a multi-plane electronic scan ultrasound probe having a rotary member mounted on the distal end of an elongated catheter and an ultrasound transducer, namely a large number of ultrasound elements positioned in a row, mounted on the rotary member. The ultrasound probe has a tilting mechanism to tilt the rotary member which in turn tilts the ultrasound transducer.

Another patent, U.S. Pat. No. 5,159,931 issued to Pinni describes an apparatus which achieves the three-dimensional reconstruction of anatomic structures by acquiring two dimensional echographic images produced by real time processing of signals that are reflected and/or scattered by the structures when they are hit by an ultrasound beam generated by a piezoelectric transducer contained within an echographic probe. In use, the sector scan transducer rotates through a 180 degree angle around the longitudinal axis of the probe.

Another example of a rotating ultrasound transducer array used in an ultrasound imaging apparatus to create a three-dimensional image can be seen in U.S. Pat. No. 5,070,879 issued to Herres. The Herres patent discloses an ultrasound imaging apparatus having a probe disposed on a longitudinal axis and ultrasound transducer elements arranged along the axis of the probe. The ultrasound array alternates between remaining stationary and oscillating about the axis of the probe in order to define a sector. In the first mode, where the array is held stationary, the transducer elements are operated successively to generate a longitudinal rectilinear scan. In the second mode, where the array is oscillated, the transducer elements are repeatedly operated to generate a transverse sector scan orthogonal to the longitudinal scan. The transducer elements are operated in one mode repeatedly at all of the transducer element positions of the other mode to generate a three-dimensional scan.

Although the generation of the three-dimensional images using ultrasound imaging apparatus which contain ultrasound arrays that are rotated about a center axis is common in the field of art, there is a need for an improved ultrasound imaging apparatus for three dimensional ultrasound imaging which utilizes an ultrasound imaging apparatus that utilizes an array which can focus in the elevation dimension and that comprises a structural make-up which limits maintenance and failure of the apparatus

SUMMARY OF THE INVENTION

It is a principal object of the present invention to provide a method and apparatus for performing three-dimensional ultrasound imaging for diagnostic procedures that utilizes a scanhead having a one, one and one-half dimensional, or two-dimensional array of ultrasound transducer elements.

It is another object of the present invention to provide a method and apparatus for performing ultrasound imaging for diagnostic procedures that utilizes an array that can focus in the elevation dimension in order to provide more flexibility and better shape of the focal region.

It is still another object of the present invention to provide a method and apparatus for performing three-dimensional ultrasound imaging having an array of ultrasound transducer elements that are swung in a concentric radius with the acoustic membrane of the apparatus, instead of rotated, thereby removing any limitations on the size of the array of transducer elements.

It is yet another object of the present invention to provide a method and apparatus for performing ultrasound imaging for diagnostic procedures having a wet module coupled to a dry module which eliminates leakage from the wet module to the dry module, and thereby eliminates damage to the dry module resulting from such leakage.

Yet another object of the present invention is to provide a method and apparatus for diagnostic ultrasound imaging having a wet module comprising an array of ultrasound transducer elements in an oil or other suitable acoustic coupling liquid and means for driving the transducer elements, a dry module comprising the electronics to power the driving means, a fluid impervious seal separating the wet module from the dry module, and a flexible printed circuit board which traverses the seal and connects the electronics to the transducer array.

It is still a further object of the present invention to provide a method and apparatus for performing diagnostic ultrasound imaging where the ultrasound imaging apparatus comprises a wet module, a dry module and a reliable seal between the wet and dry modules thereby increasing performance of the apparatus and enhancing the image quality.

It is yet another object of the present invention to provide a method and apparatus for performing diagnostic ultrasound imaging where the same continuous distance is maintained between the ultrasound transducer array and the scanning membrane of the apparatus in order to decrease acoustic reverberations during imaging.

It is yet a further object of the present invention to provide a method and apparatus for performing ultrasound imaging for diagnostic procedures which removes limitations on the size of the transducer elements while controlling the size of the wet module containing the transducer elements to ensure that the resulting apparatus is small enough to be clinically useful.

It is still another object of the present invention to provide a method and apparatus for performing three-dimensional diagnostic ultrasound imaging that utilizes a concave array of transducer elements that rotate, which as a result, requires a very small coupling area between the scanhead and the body or membrane in order to perform the imaging.

Yet another object of the present invention is to provide a method and apparatus for performing diagnostic ultrasound imaging which involves generating a succession of longitudinal scans which are stacked together to create a three-dimensional image.

In brief, a preferred embodiment the diagnostic ultrasound imaging apparatus of the present invention includes a swing shaft having a longitudinal axis, at least one ultrasound transducer element, but preferably an array of transducer elements connected to the swing shaft at a predetermined distance from its longitudinal axis, means for swinging the transducer array in a concentric radius about the longitudinal axis of the swing shaft, power means for operating the transducer array, and means for displaying the echos that are received from operating the transducer array. The apparatus preferably comprises a wet housing module and a dry housing module. The wet housing module includes the swing shaft, the ultrasound transducer array, and means for swinging the ultrasound transducer array, all of which are contained in a wet medium. The dry housing module includes the electronics for connecting the ultrasound array contained in the wet housing module to a power source and to means for displaying the echos that are received from operating the transducer array, such as computer hardware and software. The wet and dry housing modules are coupled to one another but separated by a fluid impervious seal to prevent the wet medium from leaking into the dry housing module thereby causing damage to the dry housing module. The preferred means for connecting the ultrasound transducer array contained in the wet housing module to the electronics contained in the dry housing module is in the form of a flexible printed circuit board which passes through the fluid impervious seal while still enabling the seal to remain fluid impervious. Although less reliable with respect to leakage, other means for connecting the ultrasound transducer to the electronics in the dry housing module, as described in the prior art, may also be used in the apparatus of the present invention. Finally, the ultrasound transducer array preferably comprises a one, one and one-half dimensional, or two dimensional array of ultrasound transducer elements. The array may be a phased array or a linear array with the transducer elements preferably being convex.

A second embodiment of the diagnostic ultrasound imaging apparatus of the present invention includes a first housing module having an ultrasound transducer contained in a wet medium and means for rotating the ultrasound transducer about a longitudinal axis contained therein, a second housing module having electronics for operating the ultrasound transducer and for receiving information from the ultrasound transducer contained therein where the first and second housing modules are coupled to one another but separated by a fluid impervious seal. The ultrasound transducer contained in the first housing module is connected to the electronics contained in the second housing module by a flexible printed circuit board which traverses the fluid impervious seal without breaking the fluid impervious seal that exists between the two housing modules. The transducer may comprise a phased array or linear array of ultrasound transducer elements with the transducer elements having a concave configuration.

According to a broad aspect of the present invention, there is provided a method for performing diagnostic ultrasound imaging which includes the steps of positioning an ultrasound transducer array at a predetermined distance from the longitudinal axis of the probe of an ultrasound imaging apparatus, rotating and operating the transducer array about the longitudinal axis of the probe such that the ultrasound transducer array is maintained in a concentric position with the acoustic membrane of the probe, and compiling the sequential scanning data obtained from the ultrasound transducer to create a three dimensional image. The ultrasound transducer array generates a series of sequential two-dimensional scans which are then processed with computer software to create a three-dimensional image of the object scanned.

The objectives, features and advantages of the method and apparatus for performing diagnostic ultrasound imaging of the present invention will become more apparent to those skilled in the art from the following more detailed description of the preferred embodiments of the invention made in conjunction with the accompanying drawings.

BRIEF DESCRIPTION OF THE DRAWINGS

FIG. 1 is a schematic of a partial top plan view of the apparatus for performing diagnostic ultrasound imaging of the present invention showing the wet housing module and the seal member that separates the wet housing module from the dry housing module of the apparatus.

FIG. 2 is a schematic of a partial top plan view of the apparatus for performing diagnostic ultrasound imaging of the present invention showing the wet housing module of the apparatus including the mechanical driver assembly for driving the ultrasound transducer array, and the seal member that separates the wet housing module from the dry housing module of the apparatus.

FIG. 3 is a cross-sectional view of the components contained in the wet housing module of the apparatus for performing diagnostic ultrasound imaging of the present invention taken along line 3—3 of FIG. 2.

FIG. 4 is a schematic top plan view of the apparatus for performing diagnostic ultrasound imaging of the present invention showing both the wet and dry housing modules of the apparatus and the components thereof.

DETAILED DESCRIPTION OF THE PREFERRED EMBODIMENTS

Figure 5A:
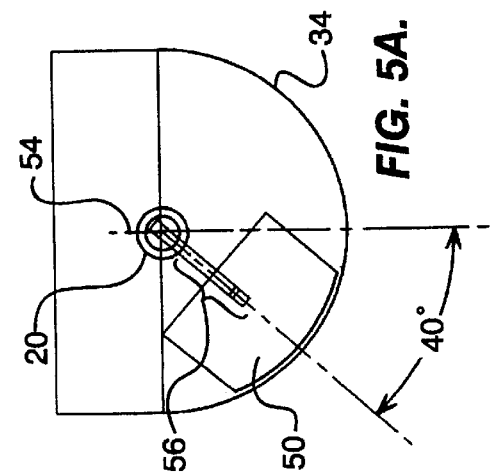
FIGS. 5A, 5B and 5C are sequential schematics showing the swinging movement of the ultrasound transducer array of the apparatus for performing diagnostic ultrasound imaging of the present invention.

Referring now to the figures, where like reference numbers refer to similar elements, FIG. 4 shows a top schematic view of the diagnostic ultrasound imaging apparatus 10 of the present invention. The diagnostic ultrasound imaging apparatus 10 includes a first (or wet) housing module 12 and a second (or dry) housing module 14 which are coupled together but separated at their juncture by a fluid impervious seal 16. The wet housing module 12 includes an ultrasound transducer array 18 which is connected to a swing (or drive) shaft 20 having a longitudinal axis. The swing shaft 20 is coupled to a motor 22 and motor reduction gear 24 which drives the swing shaft 20 to rotate. As can be later seen with reference to FIGS. 3 and 5–7, the ultrasound transducer array 18 is coupled to the swing shaft 20 via one or more bar members such that the ultrasound transducer array 18 is positioned at a predetermined distance from the swing shaft 20. Further, the wet housing module 12 is filled with an acoustic coupling liquid 26 such as jojoba bean oil or mineral oils.

The dry housing module 14 includes connectors 28 which are coupled via hard connect to a flexible printed circuit board 30. The flexible printed circuit board 30 is also coupled via hard connect to the ultrasound transducer array 18. The flexible printed circuit board 30 traverses the fluid impervious seal 16. The flexible printed circuit board 30 is centered upon entering the wet housing module 12 and then bends around the motor 22 and motor reduction gear 24, as well as the swing shaft 20, and then hard connects with the ultrasound transducer array 18. The connectors 28 are coupled to a cable assembly 32 which is in turn connected to an ultrasound scanner and motor controller (not shown). The ultrasound scanner and motor controller are used to operate the ultrasound transducer array 18 and to receive and process echo data obtained from operating the ultrasound transducer array 18. This processing is performed by utilizing computer software which sequentially stacks up a succession of two-dimensional longitudinal scans of the body or tissue taken by the ultrasound transducer array 18 to create a three-dimensional image. The portion of the flexible printed circuit board 30 which traverses the fluid impervious seal 16 is sealed within the seal 16 using epoxy or some other type of comparable glue or sealant. Finally, it should be noted that the wet housing module 12 includes an acoustic membrane 34, with which the ultrasound transducer array 18 is concentrically positioned when the ultrasound transducer array 18 is swinging about the longitudinal axis of the swing shaft 20. This configuration ensures that the spacing between the acoustic membrane 34 and the ultrasound transducer array 18 remains constant throughout the imaging process.

The connectors 28 may be multiple contact header pins or sockets or alternatively solder pads for direct cable connection. The connectors may be either surface mounted or non-surface mounted. The cable assembly is coupled to connectors 28 through corresponding mating parts. This configuration of the cable assembly 32 and connectors 28 allows a user to easily disconnect the cable assembly for repair, replacement and maintenance. The motor 22 is preferably a miniature stepping motor such as the AM1524 gearhead motor manufactured by MicroMo Electronics.

FIG. 1 shows a top view of the wet housing module of the diagnostic ultrasound imaging apparatus of the present invention. As previously described, the fluid impervious seal 16 separates the wet housing module 12 from the dry housing module. The wet housing module 12 contains a swing or drive shaft 20 which is connected to the motor reduction gear 22. The ultrasound transducer array 18 is connected to the swing or drive shaft 20 by one or more bar members (not shown) which are later shown with reference to FIGS. 2, 3, and 5–7. The wet housing module 12 is filled with an acoustic coupling liquid 26 and the ultrasound transducer array 18 is positioned in very close proximity to the acoustic membrane 34 in order to decrease ghost images and increase spatial resolution.

FIGS. 2 and 3 are more detailed schematics of the mechanical driver design used in the wet housing module 12 of the diagnostic ultrasound imaging apparatus 10 of the present invention. More specifically, FIG. 2 shows a schematic of a partial top plan view of the apparatus 10 depicting the mechanical driver assembly 36 contained in the wet housing module 12. The swing or drive shaft 20, the motor 22, and the motor gear reduction 24 all comprise part of the mechanical driver assembly 36. FIG. 2 also depicts the sweep angle 38 of the ultrasound transducer array 18. The advantages of the sweep angle 38 of the ultrasound transducer array 18 and the images produced therefrom will be further discussed with preference to FIGS. 5A through 5F.

FIG. 3 shows a cross-sectional view of the mechanical driver assembly 36 attached to the ultrasound transducer array 18 taken along line 3—3 of FIG. 2. The mechanical driver assembly 36 includes the motor 22, a precision gear head 40, and swing or drive shaft 20 all contained within a frame 42. The motor 22 is coupled to the precision gear head 40 which is in turn coupled to the motor reduction gear 24. Further, the swing or drive shaft 20 is coupled to a shaft reduction gear 44 which interconnects with the motor reduction gear 24 so that the swing or drive shaft 20 can be driven by motor 22. The ultrasound transducer array 18 is connected to the swing or drive shaft 20 by bar members 46 resulting in positioning of the ultrasound transducer array 18 at a predetermined distance from the swing or drive shaft 20. The importance of positioning the ultrasound transducer array 18 at a predetermined distance from the axis of rotation of the swing or drive shaft 20 is later described in detail with reference to FIGS. 5A through 5F. Finally, a potentiometer assembly 48 is coupled to the swing or drive shaft 20 at the end of the swing or drive shaft 20 which is opposite the shaft reduction gear 11. The potentiometer assembly 48, or other position sensor, such as a Hall-effect switch and magnet, serves as a feedback element to help control the pointing direction of the transducer.

It is contemplated that the ultrasound transducer array 18 will comprise a one, one and one-half dimensional (1.5 D) array, or two dimensional (2 D) array. A 2 D phased array has a large number of elements in both the azimuth and elevation dimensions. Therefore, 2 D arrays can focus and steer the acoustic beam in both dimensions. As a result, a 2 D array can scan a pyramidal region in real time to produce a volumetric image using parallel received processing. The 1.5 D array is similar to a 2 D array in construction but a 1 D array in operation. Like the 2 D array, the 1.5 D array contains elements along both the azimuth and elevation dimensions. With the 1.5 D array, dynamic focusing and phase correction can be implemented in both dimensions to improve image quality. However, since a 1.5 D array contains a limited number of elements in elevation, steering is not possible in that direction. Linear sequential scanning is also possible with 1.5 D arrays.

In using a 1.5 D array for linear sequential scanning, the ultrasound imaging apparatus 10 of the present invention creates a sequential series of 2-dimensional slices which are stacked together to create a 3-dimensional image. In contrast, a 2 D phased array can scan a pyramidal region in real time to produce a 3-dimensional image.

Turning now to FIG. 5, FIGS. 5A through 5C are sequential schematics showing the swinging movement of the ultrasound transducer array 18 of the apparatus 10 for performing diagnostic ultrasound imaging of the present invention. In contrast, FIGS. 5D through 5F are sequential schematics showing the rotating movement of the ultrasound transducer array of prior art apparatus for performing diagnostic ultrasound imaging. More particularly, FIGS. 5D through 5F show a rotating transducer module 50 which rotates about an axis 52 located in the middle of the transducer module 50. As the transducer module 50 rotates in a counterclockwise direction, the transducer module 50 touches the acoustic membrane 34, then moves to a position where the transducer module 50 is separated from the acoustic membrane by a constant length, and then moves away from the acoustic membrane 34, which results in the transducer module 50 being at a distance away from the acoustic membrane 34 that is six times the distance between the transducer module 50 and acoustic membrane 34 in FIG. 5E. In order to avoid hitting the acoustic membrane 34, one can reduce the size of the transducer module 50 in an effort to move the transducer module 50 away from the acoustic membrane 34. However, reducing the size of the transducer module 50 would prevent the use of a 1.5 D array because elevation dimension would be restricted which in turn would limit the focusing ability of the transducer in that dimension. Also, as the transducer module 50 moves farther from the acoustic membrane 34, the acoustic coupling liquid absorbs more of the acoustic beam because of the larger distance between the acoustic membrane 34 and the transducer module 50. Further, the physical size of the wet housing module 12 would need to be larger and ultimately could be too large to be clinically useful. Finally, acoustic reverberations exist between the transducer module 50 and the acoustic membrane 34 which decrease resolution by creating ghost images.

Figure 5B:
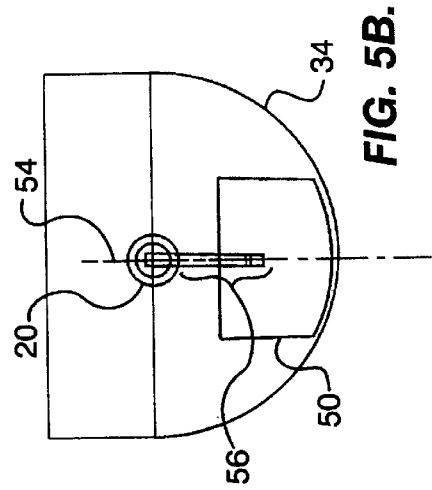
Figure 5C:
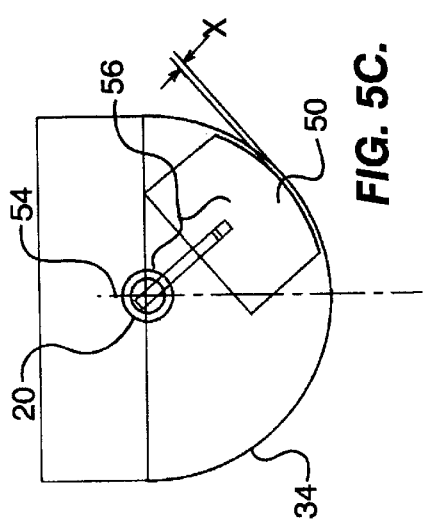
Figure 5D:
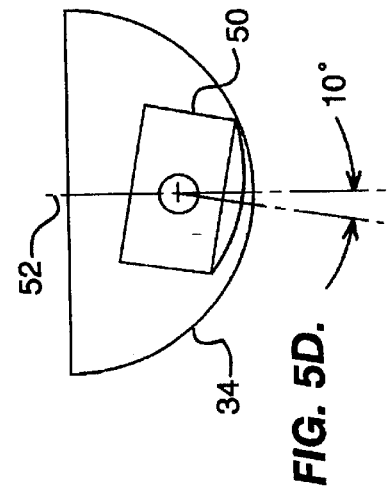
FIGS. 5D, 5E and 5F are sequential schematics showing the rotating movement of the ultrasound transducer array of prior art apparatus for performing diagnostic ultrasound imaging.
Figure 5E:
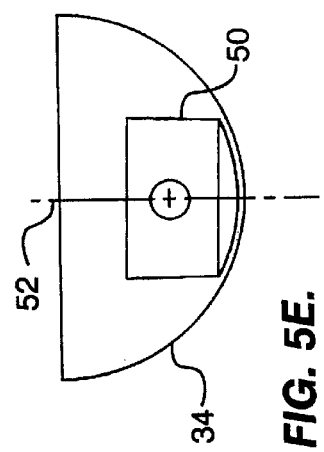
Figure 5F:
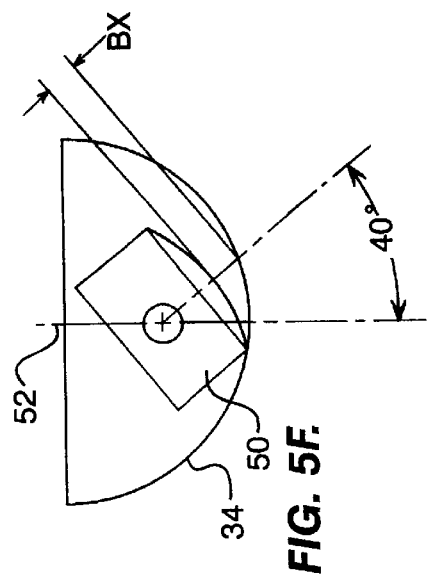

In contrast to FIGS. 5D through 5F, FIGS. 5A through 5C depict a transducer module 50 which rotates about a longitudinal axis 54 of a swing shaft 20 at a predetermined distance 56 from the swing shaft 20. This configuration results in a transducer module 50 which swings in a concentrically constant position with the acoustic membrane 34. Accordingly, the distance between the transducer module 50 and the acoustic membrane 34 in each of FIGS. 5A, 5B and 5C is constant throughout the imaging process. As a result, there are no longer any limitation on the size of the array of transducer elements. Therefore, a 1.5 D or 2 D transducer array may be used which means that the array can be focused in the elevation dimension in order to provide more flexibility and better shape of the focal region. This also results in a decrease in acoustic reverberations and an increase in resolution of the image.

Figure 6:
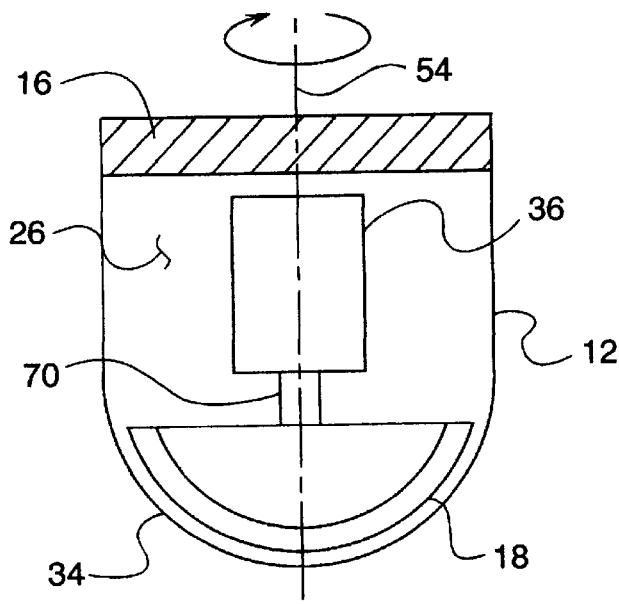
FIG. 6 is a schematic of a partial top plan view of the apparatus for performing diagnostic ultrasound imaging of the present invention showing the wet housing module, having a curved linear array ultrasound transducer, and the seal member that separates the wet housing module from the dry housing module of the apparatus.

A schematic of a partial top plan view of the apparatus for performing diagnostic ultrasound imaging of the present invention having a convex linear transducer array is shown in FIG. 6. The wet housing module 12 is coupled to the fluid impervious seal 16. The wet housing module 12 contains the mechanical driver assembly 36, the drive shaft 70, which is connected to the mechanical driver assembly 36, and the convex transducer array 18 which is connected to the drive shaft 70. The wet housing member 12 is filled with an acoustic coupling liquid 26 and also comprises the acoustic membrane 34 which is the membrane of the apparatus 10 that is used to scan the patient. The method for preforming ultrasound imaging with this type of wet housing module configuration involves rotating the convex transducer array 18 about the acoustic membrane 34 by rotating the drive shaft 70 which is driven by the mechanical driver assembly 36.

Figure 7:
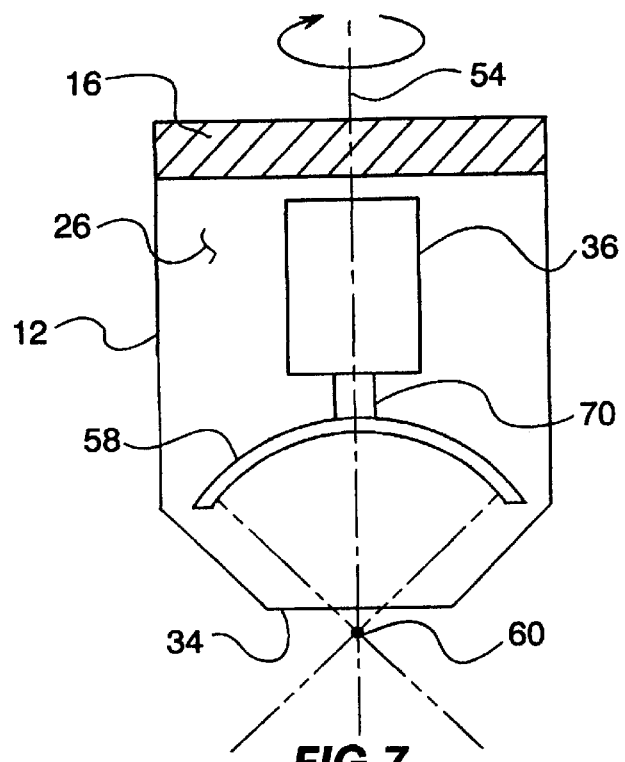
FIG. 7 is a schematic of a partial top plan view of the apparatus for performing diagnostic ultrasound imaging of the present invention showing the wet housing module, having a concave linear array ultrasound transducer, and the seal member that separates the wet housing from the dry housing module of the apparatus.

Another embodiment of the ultrasound imaging apparatus of the present invention showing a schematic of a partial top plan view of the apparatus having a concave linear transducer array is illustrated in FIG. 7. Again, as in FIG. 6, the wet housing module 12 is coupled to the fluid impervious seal 16 which separates the wet housing module 12 from the dry housing module (not shown). The wet housing module 12 contains the mechanical driver assembly 36, the drive shaft 70, which is driven by the mechanical driver assembly 36, and the concave linear transducer array 58 which is connected to the drive shaft 70. The wet housing module is filled with an acoustic coupling fluid 26. Further, as previously described in FIG. 6, the concave linear array 58 is directly coupled to the drive shaft 70 and thereby rotates about its own center longitudinal axis when in use. In utilizing a concave linear transducer array 58, the beams from each ultrasound transducer element pass through the acoustic membrane 34 and converge at a set point 60. This type of concave transducer configuration is particularly useful in those applications where ultrasound imaging needs to be performed in a small confined area, such as the heart, where it is necessary to avoid hitting the lungs and ribs with ultrasound beams.

While preferred forms of the invention have been shown in the drawings and described, since variations in the preferred forms will be apparent to those skilled in the art, the invention should not be construed as limited to the specific form shown and described, but instead is as set forth in the following claims.

We claim:

1. An apparatus for ultrasound imaging comprising:
   a first housing module;
   a second housing module connected to said first housing module;
   a fluid impervious seal separating said first and second housing modules;
   at least one ultrasound transducer contained in said first housing module; and
   a flexible printed circuit board contained within said first and second housing modules which traverses the fluid impervious seal separating the first and second housing modules, said flexible printed circuit board being connected to said at least one ultrasound transducer contained in said first housing module and to means for providing power contained in said second housing module.

2. The apparatus of claim 1 further comprising:
   a swing shaft having a longitudinal axis contained in said first housing module; and
   means for swinging said at least one ultrasound transducer about the longitudinal axis of said swing shaft at a predetermined distance from the swing shaft contained in said first housing module.

3. The apparatus of claim 2 wherein said means for swinging the ultrasound transducer comprises:
   means for connecting said ultrasound transducer to the swing shaft such that said ultrasound transducer is positioned at a predetermined distance from the swing shaft; and
   drive means for rotating said swing shaft about its longitudinal axis.

4. The apparatus of claim 3 wherein said first housing module is filled with an acoustic coupling liquid.

5. The apparatus of claim 1 wherein said at least one ultrasound transducer comprises a single convex transducer.

6. The apparatus of claim 1 wherein said at least one ultrasound transducer comprises a linear array of a plurality of convex transducer elements.

7. The apparatus of claim 1 wherein said at least one ultrasound transducer comprises a concave transducer element.

8. The apparatus of claim 1 wherein said at least one ultrasound transducer comprises a linear array of a plurality of concave transducer elements.

9. The apparatus of claim 1 wherein said linear array is a phased array.

10. The apparatus of claim 1 further comprising:
- a rotatable shaft having a longitudinal axis contained in said first housing module wherein said at least one ultrasound transducer is connected to said rotatable shaft; and
- means for rotating said rotatable shaft contained in said first housing module.

11. The apparatus of claim 10 wherein said first housing module is filled with an acoustic coupling liquid.

12. The apparatus of claim 10 wherein said at least one ultrasound transducer comprises a concave transducer element.

13. The apparatus of claim 10 wherein said at least one ultrasound transducer comprises a linear array of concave transducer elements arranged along the axis of said rotatable shaft.

14. The apparatus of claim 13 wherein said linear array is a phased array.

* * * * *